United States Patent [19]

Abdulla et al.

[11] 4,133,956

[45] Jan. 9, 1979

[54] PREPARATION OF BENZOYLUREAS

[75] Inventors: Riaz F. Abdulla, Greenfield; Norman H. Terando, Indianapolis, both of Ind.

[73] Assignee: Eli Lilly and Company, Indianapolis, Ind.

[21] Appl. No.: 819,639

[22] Filed: Jul. 27, 1977

[51] Int. Cl.² .................. C07D 241/20; C07D 241/06
[52] U.S. Cl. .................................. 544/336; 544/408; 544/409; 544/353; 544/356; 260/553 A; 546/306
[58] Field of Search ........ 260/250 BN, 250 Q, 295 E, 260/553 C, 553 A; 544/336, 408, 409, 353, 356

[56] References Cited

U.S. PATENT DOCUMENTS 3,748,356  7/1973  Wellinga et al. ................ 260/553 E

*Primary Examiner*—Jose Tovar
*Attorney, Agent, or Firm*—Leroy Whitaker; Arthur R. Whale

[57] ABSTRACT

Benzoylureas are prepared from a benzamide, an alkyllithium, a phenyl chloroformate, and an amine. Two reaction sequences are described. The benzoylureas obtained by the process are useful as insecticides.

20 Claims, No Drawings

PREPARATION OF BENZOYLUREAS

BACKGROUND OF THE INVENTION

1. Field of the Invention

This invention relates to a process for the preparation of benzoylureas. The products of the process are insecticides.

2. Description of the Prior Art

Wellinga et al. U.S. Pat. No. 3,748,356 describes benzoylureas having a phenyl or pyridyl substituent on the $N^3$-nitrogen. Such ureas are described as insecticides. Several methods for the preparation of the compounds are described but none involves the steps of the presently claimed method.

Belgian Pat. No. 833,288 discloses benzoylureas wherein the $N^3$-nitrogen bears a pyrazine or benzopyrazine substituent. Such compounds are taught to be insecticidal. The methods of preparation taught in the Belgian patent do not involve the steps of the presently claimed method.

SUMMARY OF THE INVENTION

We have now discovered a method for the preparation of benzoylureas such as those disclosed in U.S. Pat. No. 3,748,356 and Belgian Pat. No. 833,288, which comprises the reaction of a benzamide, a $C_1$–$C_7$ alkyllithium, a phenyl chloroformate and an amine. In one embodiment of the reaction, the benzamide is treated with the alkyllithium and a phenyl chloroformate in an inert solvent at a temperature of from about −80° to about −40° C. to form an intermediate urethane, the intermediate urethane is treated with an amine in an inert solvent at about −80° to about −40° C., and the temperature is slowly raised to from about 50° to about 100° C. to obtain the desired benzoylurea. In a second embodiment of the reaction, the benzamide is treated with the alkyllithium in an inert solvent at a temperature from about −80° to about −40° C. and the lithium salt so obtained is then treated with a carbamate at a temperature of about −80° to about −40° C., and the mixture is allowed to warm to from about 20° to about 40° C. to obtain the desired benzoylurea. The carbamate is obtained by the reaction of an amine with a phenyl chloroformate.

DESCRIPTION OF THE PREFERRED EMBODIMENT

The compounds to be prepared by our process are those having the formula

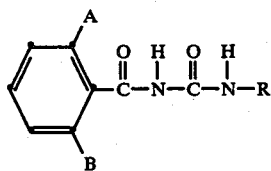

wherein
A is chloro, fluoro, bromo, methyl or trifluoromethyl;
B is hydrogen, chloro, fluoro, bromo, methyl or trifluoromethyl;
R is

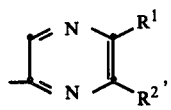

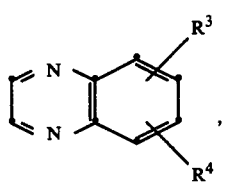

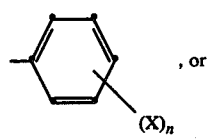

$R^1$ is hydrogen, halo, $C_1$–$C_6$ alkyl, halo($C_1$–$C_4$alkyl), cyano,

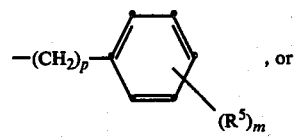

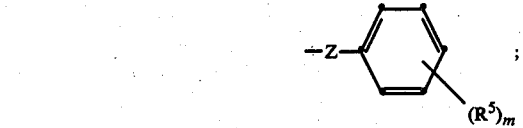

$R^2$ is hydrogen, halo, methyl, ethyl, cyano or halo($C_1$–$C_4$) alkyl;
$R^3$ and $R^4$ are the same or different and are hydrogen, halo, $C_1$–$C_6$ alkyl, cyano or halo($C_1$–$C_4$) alkyl;
$R^5$ is halo, halo($C_1$–$C_4$)alkyl, $C_1$–$C_6$ alkyl, cyano or phenyl;
X is halo or $C_1$–$C_4$ alkyl;
y is halo;
Z is oxygen or sulfur;
n is 0, 1 or 2;
p is 0 or 1; and
m is 0, 1, 2, or 3.

The preferred compounds are those in which B is other than hydrogen. Especially preferred are those compounds wherein both A and B are chloro.

In the above description the terms used have their usual meaning in the chemical art. The alkyl groups may be straight or branched chain. Halo refers to fluoro, chloro, bromo, or iodo.

In accordance with one embodiment of our process, compounds of formula I are prepared in accordance with the following reaction scheme:

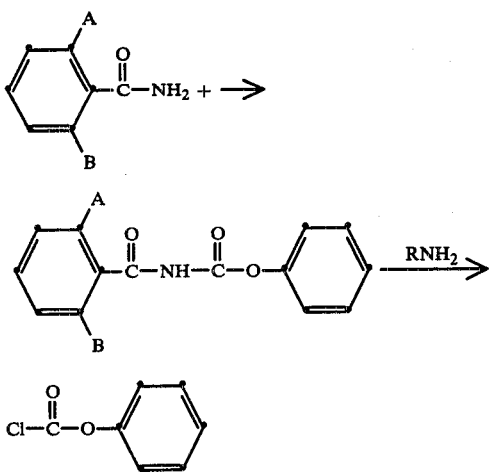

In the above scheme the benzamide used in step 1 and the amine used in step 2 are selected to give the desired benzoylurea. The preferred benzamides are those in which A and B are chloro, fluoro or bromo with the dichlorobenzamide being most preferred. The preferred amine is a pyrazinyl amine, a benzopyrazinyl amine, or a phenyl amine.

Phenyl chloroformate and especially 4-nitrophenyl chloroformate are preferred for use in the first step of the process. However, other phenyl chloroformates such as 2,4-dinitrophenyl chloroformate and 4-trifluoromethylphenyl chloroformate may be used. The first step is conducted in an inert solvent which remains liquid at the low temperatures employed. Examples of suitable solvents include tetrahydrofuran and diethyl ether. The reaction is conducted at a temperature of from about −80° to about −40° C. and preferably at a temperature of from about −75° to about −65° C.

The alkyllithium employed may be any alkyllithium containing from 1 to 7 carbon atoms. The preferred alkyllithium is n-butyllithium.

In the preferred method of carrying out the reaction, the alkyllithium is added to the amide in the solvent at a temperature of about −80° to about −40° C. over a period of about 10 to 15 minutes and the mixture is stirred for about 30 minutes at the low temperature. The phenyl chloroformate in the solvent is then added at the low temperature over a period of about 15 to 20 minutes and the mixture is stirred in the cold for a time of from about 2 to about 6 hours.

In the second step, the amine in an inert solvent such as tetrahydrofuran, diethyl ether or toluene is added over a period of from about 5 to about 20 minutes to the urethane from the first step maintained at a temperature of from about −80° to about −40° C. The temperature of the mixture is allowed to rise and then the mixture is heated at a temperature of from about 50° to about 100° C., preferably about 50° to about 65° C., for a period of from about 4 to about 24 hours to obtain the desired benzoylurea.

The benzamides, phenyl chloroformates, anilines, aminopyridines, and lithium compounds for use in the process are readily available or easily synthesized by those skilled in organic chemistry. The pyrazines and benzopyrazines (quinoxalines) may be prepared by usual chemical procedures.

One of the intermediates, 2-amino-5-chloropyrazine is prepared following the general procedure of Palamidessi and Bernardi, J. Org. Chem. 29, 2491 (1964), wherein methyl 2-amino-3-pyrazinylcarboxylate is allowed to react with chlorine in acetic acid to yield methyl 2-amino-5-chloro-3-pyrazinylcarboxylate. This ester is hydrolyzed with aqueous sodium hydroxide to yield 2-amino-3-carboxy-5-chloropyrazine, which is then heated in tetrahydronaphthalene and decarboxylated to yield the desired 2-amino-5-chloropyrazine.

Another intermediate, 2-amino-5,6-dichloropyrazine, is prepared by allowing 2-amino-6-chloropyrazine to react with N-chlorosuccinimide in chloroform to yield a mixture of 2-amino-5,6-dichloropyrazine, 2-amino-3,6-dichloropyrazine, and 2-amino-3,5,6-trichloropyrazine. The mixture is then separated by column chromatography and the desired 2-amino-5,6-dichloropyrazine is obtained.

The 2-amino-5-phenylpyrazine necessary for this work is prepared according to the procedure of Lont et al., Rec. Trav. Chim. 92, 455 (1973), and references therein.

Other 2-amino-5(or 6)-substituted pyrazines useful in preparing the novel final compounds of this invention are prepared utilizing oxime derivatives of certain ketones. Thus, 2-oxopropanal 1-oxime and 2-oxobutanal 1-oxime are prepared from ethyl acetoacetate and ethyl propioacetate, respectively, following the procedure of Meyer et al., Chem. Ber. 11, 695 (1878). Other oxime intermediates are prepared from such ketones as acetophenone, 2,4-dimethylacetophenone, p-chloroacetophenone, and benzyl methyl ketone, following the general procedure of Claisen et al., Chem. Ber. 20, 2194 (1887). Still other oxime intermediates are prepared from ketones such as p-methoxypropiophenone, p-bromobutyrophenone, p-bromopropiophenone, and methyl neopentyl ketone, following the general procedure of Hartung et al., J. Am. Chem. Soc. 51, 2262 (1929).

Yet another oxime intermediate is prepared from t-butyl methyl ketone, which is first transformed into t-butylglyoxal using the procedure of Fuson et al., J. Am. Chem. Soc. 61, 1938 (1939). The t-butylglyoxal, in aqueous solution at pH 4–5, is allowed to react with acetone oxime (commercially available) at about room temperature for about two days. The reaction product mixture is worked up by extracting it with ether, and the t-butylglyoxal oxime is isolated from the ether extract as colorless needles having a melting point of about 50–52° C.

The intermediate 2-amino-5-methylpyrazine is prepared stepwise, starting with 2-oxopropanal 1-oxime. This oxime is allowed to react with aminomalononitrile tosylate [prepared by the method of Ferris et al., J. Am. Chem. Soc. 88, 3829 (1966)], to yield 2-amino-3-cyano-5-methylpyrazine 1-oxide. The pyrazine 1-oxide prepared in this manner is allowed to react with phosphorous trichloride to yield 2-amino-3-cyano-5-methylpyrazine. This 2-amino-3-cyano-5-methylpyrazine is hydrolyzed with aqueous sodium hydroxide to yield 2-amino-3-carboxy-5-methylpyrazine, which, when heated in tetrahydronaphthalene, is decarboxylated to yield the desired 2-amino-5-methylpyrazine.

Following the same general procedure set forth in the preceding paragraph, and starting with 2-oxobutanal 1-oxime, there is obtained 2-amino-5-ethylpyrazine.

Another intermediate pyrazine compound, 2-amino-5-(4-bromophenyl)-6-methylpyrazine is synthesized starting with 1-(4-bromophenyl)-1,2-propanedione 2- oxime, which oxime is obtained by the same general procedure of Hartung et al., supra. This oxime is allowed to react with aminomalononitrile tosylate, and the product, the substituted pyrazine 1-oxide, is allowed to react with phosphoruc trichloride in tetrahydrofuran, according to the procedure of Taylor et al., *J. Org. Chem.* 38, 2817 (1973), to yield 2-amino-3-cyano-5-(4-bromophenyl)-6-methylpyrazine. This product is then hydrolyzed in sodium hydroxide and ethylene glycol and the 2-amino-3-carboxy-5-(4-bromophenyl)-6-methylpyrazine so obtained is decarboxylated by heating in tetrahydronaphthalene to yield 2-amino-5-(4-bromophenyl)-6-methylpyrazine.

Another intermediate, 2-amino-5,6-dimethylpyrazine is prepared from 2-chloro-5,6-dimethylpyrazine, which in turn is prepared according to the procedure of Karmas et al., *J. Am. Chem. Soc.* 74, 1580–1584 (1952).

Still other pyrazine intermediate compounds can be prepared starting with 2,5-dichloropyrazine, which itself can be prepared by the procedure of Palamidessi and Bernardi, *J. Org. Chem.* 29, 2491 (1964). This 2,5-dichloropyrazine can be used as the starting material for the phenoxy or phenylthio substituted pyrazine intermediates, or the corresponding substituted phenoxy or phenylthio substituted pyrazine intermediates. Thus, as a general procedure, 2,5-dichloropyrazine can be allowed to react with an equivalent of phenoxide or thiophenoxide ion in a suitable solvent such as ethanol, t-butanol, dimethylformamide, acetonitrile, or the like, at a temperature in the range of from about 0° to about 120° C., to yield the corresponding 2-chloro-5-phenoxy-(or phenylthio)pyrazine. The 2-chloro-5-phenoxy(or phenylthio)pyrazine can be converted to the corresponding 2-amino-5-phenoxy(or phenylthio)pyrazine by reaction with ammonium hydroxide at a temperature in the range of about 150°–200° C. in a high pressure reaction vessel for a time sufficient to give substantially complete conversion. The 2-amino-5-phenoxy(or phenylthio)pyrazine obtained in this manner can then be used to prepare the 1-substituted benzoyl)-3-[5-phenoxy(or phenylthio)-2-pyrazinyl]ureas. Homologous phenoxy or phenylthio compounds can be prepared in the same general manner.

The 2-aminoquinoxalines, which are simply aminobenzopyrazines, are also prepared by methods well known in the art. For example, 2-aminoquinoxaline is prepared by allowing the commercially available 2-chloroquinoxaline to react with ammonia in a suitable solvent such as ethanol at the temperature of a steam bath.

Other intermediate quinoxalines are prepared starting with the appropriate o-phenylenediamines, which may or may not be commercially available.

Some of the o-phenylenediamines which are not commercially available are readily prepared from the corresponding dinitroanilines by hydrogenation. The hydrogenations are carried out by using anhydrous hydrazine in the presence of 5% ruthenium on carbon (Engelhard Industries) in a suitable solvent, such as commercial absolute ethanol, at a temperature of about 55°–70° C. Thus, for example, 5-cyano-3-nitro-o-phenylenediamine is readily prepared by the selective hydrogenation of 4-cyano-3,5-dinitroaniline in the presence of 5% ruthenium on carbon in ethanol as solvent, together with anhydrous hydrazine. Following the same general procedure 3-nitro-5-trifluoromethyl-o-phenylenediamine is prepared from 2,6-dinitro-4-trifluoromethylaniline.

Other o-phenylenediamines useful in preparing the quinoxaline intermediates for synthesizing the novel compounds of this invention are prepared by reduction of commercially available o-nitroanilines through the use of 5% palladium on carbon catalyst in a low pressure hydrogenation apparatus. For example, 2-nitro-4-trifluoromethylaniline is reduced in this manner to yield 4-trifluoromethyl-o-phenylenediamine.

The 2-amino-6-chloroquinoxaline and 2-amino-7-chloroquinoxaline are prepared by methods well known in the art, and elegantly described in *The Chemistry of Heterocyclic Compounds, Condensed Pyridazine and Pyrazine Rings, Part III, Quinoxalines,* Chapter XXIV et seq., page 203 et seq., by J. C. E. Simpson, [Arnold Weissberger, Consulting Editor, Interscience Publishers, Inc., New York (1953)]. Thus, 3,4-diaminochlorobenzene is allowed to react with glyoxylic acid to yield a mixture of 6-chloro-2-hydroxyquinoxaline and 7-chloro-2-hydroxyquinoxaline. The mixture in turn is allowed to react with phosphorous oxychloride to yield a mixture of 2,6-dichloroquinoxaline and 2,7-dichloroquinoxaline. The mixture is allowed to react with anhydrous ammonia in a suitable solvent, dimethylsulfoxide being the solvent of choice, to yield a mixture of 2-amino-6-chloroquinoxaline and 2-amino-7-chloroquinoxaline.

With the above background on starting materials in mind, our process for the preparation of benzoylureas will now be illustrated by the following examples which are not to be interpreted as limiting our process.

EXAMPLE 1

1-(2,6-Dichlorobenzoyl)-3-[6-methyl-5-(4-bromophenyl)-2-pyrazinyl]urea

A solution of 304 mg. of 2,6-dichlorobenzamide and 25 ml. of dry tetrahydrofuran was placed in a 3-necked, 50 ml. round bottomed flask. With mechanical stirring and under nitrogen the solution was cooled to about −72° C. in a dry ice/acetone bath. To this solution was added 0.6 ml. of n-butyllithium reagent over a period of 5 minutes. After the addition was complete, the mixture was stirred for 30 minutes at about −72° C. A solution of 268 ml. of 4-nitrophenyl chloroformate in 8 ml. of dry tetrahydrofuran was added dropwise over a period of 15 to 20 minutes. A pale yellow solution formed. After the addition was complete, the mixture was stirred for 30 minutes at about −72° C. giving a colorless solution. The cooling bath was adjusted so that the temperature was raised to between −40° C. and −30° C. and stirring was continued for 3 hours. The mixture was recooled to approximately −72° C. and a solution of 351 mg. of 2-amino-5-(4-bromophenyl)-6-methylpyrazine in 6 ml. of dry tetrahydrofuran was added dropwise over a period of 10 minutes. The cooling bath was removed allowing the mixture to warm to room temperature. The mixture was then heated at 50° C. for 16 hours to complete the reaction. The solvent was removed in vacuo and the residue was taken up in ethyl acetate. The ethyl acetate solution was washed 5 times with aqueous sodium carbonate solution and twice with salt water. The solvent was again evaporated and the residue dissolved in 2 ml. of tetrahydrofuran and chromatographed over silica gel using 4:1 benzene/tetrahydrofuran. The product from chromatography was dissolved in tetrahydrofuran and the solution concentrated in vacuo to an oil. Ether was added and the solution was cooled to precipitate in 2 crops 240 mg. of product.

Recrystallization from tetrahydrofuran/ether yielded 132 mg. of product, m.p. 225°–227° C. An additional 69 mg. of product was obtained from the filtrate by preparative thin-layer chromatography.

EXAMPLE 2

1-(2,6-Dichlorobenzoyl)-3-[5-(4-chlorophenyl)-2-pyrazinyl]urea

The procedure of Example 1 was repeated using 273.5 mg. of 2-amino-5-(4-chlorophenyl)pyrazine in place of the 2-amino-5-(4-bromophenyl)-6-methylpyrazine. There was obtained 222 mg. of product, m.p. 245°–249° C.

EXAMPLE 3

1-(2,6-dichlorobenzoyl)-3-[5-(3-trifluoromethylphenyl)-6-methyl-2-pyrazinyl]urea The procedure of Example 1 was repeated employing 336.8 mg. of 2-amino-5-(3-trifluoromethylphenyl)-6-methylpyrazine instead of the 2-amino-5-(4-bromophenyl)-6-methylpyrazine. The product from the silica gel column was subjected to preparative thin-layer chromatography to give a viscous oil which on standing crystallized to a white solid. The solid was triturated with cold ether and the white solid collected by filtration to give a first crop of 62 mg. of product, m.p. 182°–185° C. The filtrate was concentrated and allowed to evaporate in a hood to give a yellow oil. Crystallization of the oil from ether gave 102 mg. of white solid as a second crop of product. Total yield was 164 mg.

EXAMPLE 4

1-(2,6-dichlorobenzoyl)-3-(6-trifluoromethyl-2-pyrazinyl)urea

The procedure of Example 1 was repeated using 217 mg. of 2-amino-6-trifluoromethylpyrazine instead of the 2-amino-5-(4-bromophenyl)-6-methylpyrazine. The product was worked up as in Example 3. The oil which was obtained from the preparative thin-layer chromatography crystallized upon standing at room temperature. The crude solid was triturated with cold ether and the white crystalline solid so obtained was collected by filtration to give 144 mg. of product, m.p. 188°–192° C.

EXAMPLE 5

1-(2,6-dichlorobenzoyl)-3-(3-trifluoromethylphenyl)urea

A solution of 0.912 grams of 2,6-dichlorobenzamide in 75 ml. of dry tetrahydrofuran was placed in a 3-necked, 250 ml. round bottomed flask. The solution was cooled to about −72° C. with a dry ice/acetone bath. To the mixture was added 1.8 ml. of n-butyllithium solution over a 5-minute period. The mixture was allowed to stand for 30 minutes at −75° C. to −70° C. A solution of 0.804 grams of 4-nitrophenyl chloroformate in 24 ml. of dry tetrahydrofuran was added over a period of 30 minutes at about −72° C. The mixture was allowed to stand an additional 30 minutes in the cold at which time it became colorless. The solution was warmed to −40° C. and held at that temperature for 2.75 hours. The mixture was cooled again to about −72° C. and a solution of 0.64 grams of 3-aminobenzotrifluoride in 25 ml. of dry tetrahydrofuran was added over 10 minutes. The solution was allowed to warm to room temperature and was then heated at 50° C. for 16 hours. The solvent was removed and the residue was dissolved in 10 ml. of ether. The solution was washed with 1 N sodium carbonate solution, dried over magnesium sulfate and the solvent again removed. The residue was triturated under ether to give 0.6 grams of a white crystalline solid melting above 200° C.

Analysis Calcd: C, 47.77; H, 2.41; N, 7.43. Found: C, 46.85; H, 2.62; N, 7.20.

EXAMPLE 6

1-(2,6-dichlorobenzoyl)-3-(4-trifluoromethylphenyl)urea

To a solution of 0.912 grams of 2,6-dichlorobenzamide in 75 ml. of dry tetrahydrofuran was added 1.8 ml. of 2.4 M n-butyllithium reagent at −30° C. in one shot. To this mixture was added 0.804 grams of 4-nitrophenyl chloroformate in 25 ml. of dry tetrahydrofuran at −40° C. over a 10-minute period. The pale yellow solution which resulted was stirred until it became colorless (about 5 minutes). To the solution maintained at −35° to −30° C. was added over 5 minutes a solution of 0.8 grams of 4-aminobenzotrifluoride in 25 ml. of dry tetrahydrofuran. The solution was heated under reflux (about 60° C.) for 4 hours. The mixture was diluted with 300 ml. of ether and washed 5 times with sodium carbonate solution, dried and the solvent removed. Crystallization from ether/hexane gave 0.72 grams of product, m.p. 205° C. (not sharp).

Analysis Calcd: C, 47.75; H, 2.39; N, 7.43. Found: C, 47.50; H, 2.29; N, 7.40.

In another embodiment of the reaction, the reactants are combined in a different sequence. As a first step, the benzamide is treated with a $C_1$–$C_7$ alkyllithium in an inert solvent at a temperature of about −80 to about −40° C. to obtain the lithium salt. This step is conducted in the same manner as the first step in the first embodiment of the process. Here, too, the preferred alkyllithium is n-butyllithium. The lithium salt is then treated at −80 to −40° C. with a carbamate which is the product of the reaction of a phenyl chloroformate with an amine, $RNH_2$. The reaction mixture is stirred at the low temperature for a period of about thirty minutes to about six hours, and the mixture is then allowed to warm to a temperature of from about 20 to about 40° C. for a period of from about one to about twenty-four hours to obtain the desired benzoylurea. Suitable solvents for this step include tetrahydrofuran, diethyl ether and toluene.

The reactants employed in this second embodiment are the same as the reactants employed in the first embodiment. The second embodiment of our process is preferred. It will be illustrated by the following example.

EXAMPLE 7

1-(2,6-dichlorobenzoyl)-3-(4-trifluoromethylphenyl)urea

To a solution of 1.9 g. of 2,6-dichlorobenzamide in 75 ml. of dry tetrahydrofuran at a temperature of −70 to −75° C. was added 5.0 ml. of n-butyllithium solution in one batch. The solution was then treated with 3.26 g. of N-(p-trifluoromethylphenyl)-O-(p-nitrophenyl)carbamate in 25 ml. of dry tetrahydrofuran at −75° C. for one-half hour. The solution was allowed to warm to −30° C., where it was held for one hour and then allowed to warm to room temperature. Thin-layer chromatography showed the desired product had formed.

The product was isolated as described in Example 6 to obtain 2.20 g. melting at 200° C. (not sharp).

We claim:

1. A method for the preparation of a benzoylurea having the formula

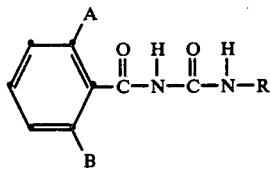

which comprises (a) treating a benzamide having the formula

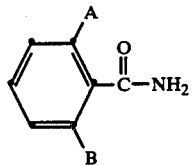

with a $C_1$–$C_7$ alkyllithium and a phenyl chloroformate in an inert solvent at about −80 to about −40° C. to form an intermediate urethane; and (b) treating the intermediate urethane with an amine having the formula

R—NH$_2$ in an inert solvent at about −80 to about −40° C. and slowly raising the temperature of the mixture and heating at about 50° to about 100° C. to obtain the desired benzoylurea; wherein A is chloro, fluoro, bromo, methyl or trifluoromethyl;

B is hydrogen, chloro, fluoro, bromo, methyl or trifluoromethyl;

R is

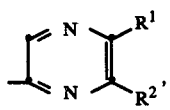

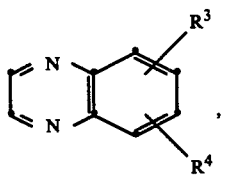

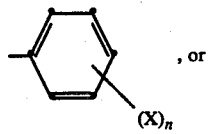

, or

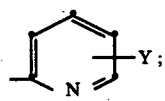

$R^1$ is hydrogen, halo, $C_1$–$C_6$ alkyl, halo($C_1$–$C_4$ alkyl), cyano,

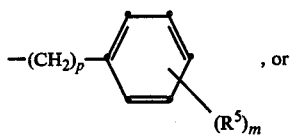, or

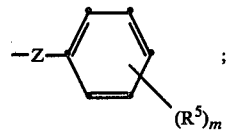;

$R^2$ is hydrogen, halo, methyl, ethyl, cyano or halo($C_1$–$C_4$)alkyl;

$R^3$ and $R^4$ are the same or different and are hydrogen, halo, $C_1$–$C_6$ alkyl, cyano or halo($C_1$–$C_4$)alkyl;

$R^5$ is halo, halo($C_1$–$C_4$)alkyl, $C_1$–$C_6$ alkyl, cyano or phenyl;

X is halo or $C_1$–$C_4$ alkyl;

y is halo;

Z is oxygen or sulfur;

n is 0, 1 or 2;

p is 0 or 1; and m is 0, 1, 2, or 3.

2. A method as in claim 1 wherein B is other than hydrogen.

3. A method as in claim 1 wherein R is

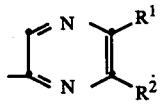

4. A method as in claim 3 wherein B is other than hydrogen.

5. A method as in claim 1 wherein R is

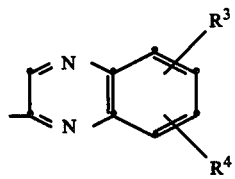

6. A method as in claim 5 wherein B is other than hydrogen.

7. A method as in claim 1 wherein R is

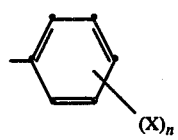

8. A method as in claim 7 wherein B is other than hydrogen.

9. A method as in claim 1 wherein the temperature of step a) is from about −75 to about −65° C. and the final temperature of step b) is about 50 to about 65° C.

10. A method as in claim 1 wherein the alkyllithium is n-butyllithium.

11. A method as in claim 1 wherein both A and B are chloro.

12. A method for the preparation of a benzoylurea having the formula

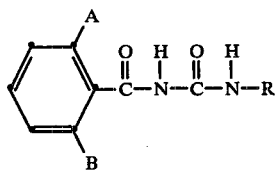

which comprises (a) treating a benzamide having the formula

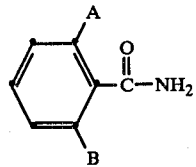

with a $C_1-C_7$ alkyllithium in an inert solvent at about $-80$ to about $-40°$ C. to form the lithium salt; and (b) treating the lithium salt with a carbamate from an amine having the formula $RNH_2$ and a phenyl chloroformate, said treatment being conducted in an inert solvent at a temperature of about $-80$ to about $-40°$ C. and slowly raising the temperature to from about 20 to about $40°$ C. to obtain the desired benzoylurea; wherein A is chloro, fluoro, bromo, methyl or trifluoromethyl;

B is hydrogen, chloro, fluoro, bromo, methyl or trifluoromethyl;

R is

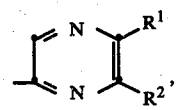

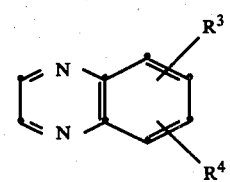

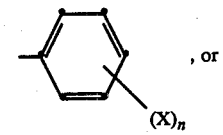

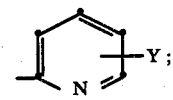

$R^1$ is hydrogen, halo, $C_1-C_6$ alkyl, halo($C_1-C_4$ alkyl), cyano,

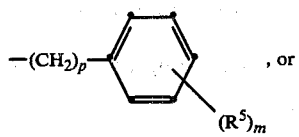

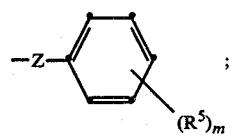

$R^2$ is hydrogen, halo, methyl, ethyl, cyano or halo($C_1-C_4$)alkyl;

$R^3$ and $R^4$ are the same or different and are hydrogen, halo, $C_1-C_6$ alkyl, cyano or halo($C_1-C_4$)alkyl;

$R^5$ is halo, halo($C_1-C_4$)alkyl, $C_1-C_6$ alkyl, cyano or phenyl;

X is halo or $C_1-C_4$ alkyl;

y is halo;

Z is oxygen or sulfur;

n is 0, 1 or 2;

p is 0 or 1; and m is 0, 1, 2, or 3.

13. A method as in claim 12 wherein B is other than hydrogen.

14. A method as in claim 1 wherein R is

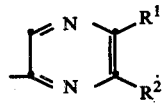

15. A method as in claim 14 wherein B is other than hydrogen.

16. A method as in claim 12 wherein R is

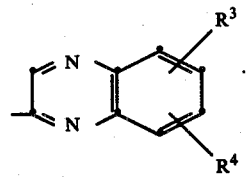

17. A method as in claim 16 wherein B is other than hydrogen.

18. A method as in claim 12 wherein R is

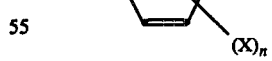

19. A method as in claim 18 wherein B is other than hydrogen.

20. A method as in claim 12 wherein both A and B are chloro.

* * * * *